United States Patent

Galey et al.

[11] Patent Number: 5,929,112
[45] Date of Patent: Jul. 27, 1999

[54] DERIVATIVES OF N,N'-DI (CARBOXYALKYL) ALKYLENE DI-OR TRIAMINE

[75] Inventors: Jean-Baptiste Galey, Aulnay-Sous-Bois; Sylvie Genard, Paris, both of France

[73] Assignee: L'Oreal, Paris, France

[21] Appl. No.: 08/681,438

[22] Filed: Jul. 23, 1996

[30] Foreign Application Priority Data

Jul. 26, 1995 [FR] France ................................. 95 09119

[51] Int. Cl.⁶ ..................... A61K 31/235; A61K 31/195; C07C 227/00; C07C 229/00
[52] U.S. Cl. ......................... 514/533; 514/566; 560/38; 560/39; 562/448; 562/443
[58] Field of Search ..................... 514/533, 566; 560/39, 38; 562/448, 443

[56] References Cited

U.S. PATENT DOCUMENTS 4,528,196  7/1985  Pitt .
5,342,604  8/1994  Wilson et al. .................... 424/1.65

FOREIGN PATENT DOCUMENTS 367 223   5/1990  Japan .
94/11338  5/1994  WIPO .

OTHER PUBLICATIONS

Chem, Abst. 88:95587; Miller et al., Inorg. Chem. (1978), 17, (3), 774–6.

Chem. Abst. 79:25122; Maricondi et al. Inorg. Chem. (1973), 12(7), 1524–8.

Martell, et al: "Development of Iron Chelators for Cooley's Anemia",pp. 218–221, Inorganica Chimica Acta.,(ICHAA3, 00201693); 87; vol. 138 (3) pp. 215–230.

Enomoto et al., (Chem. Abstra. 123:120345, JP 07116889) 1995.

*Primary Examiner*—S. Mark Clardy
*Assistant Examiner*—Sabiha N. Qazi
*Attorney, Agent, or Firm*—Nixon & Vanderhye, P.C.

[57] ABSTRACT

The derivatives of N,N'-di(aralkyl)-N,N'-di(carboxyalkyl) alkylene di- or triamine and N-(aralkyl)-N'-(carboxyalkyl)-N'N'-di(carboxyalkyl) alkylene di- or triamine of the formula:

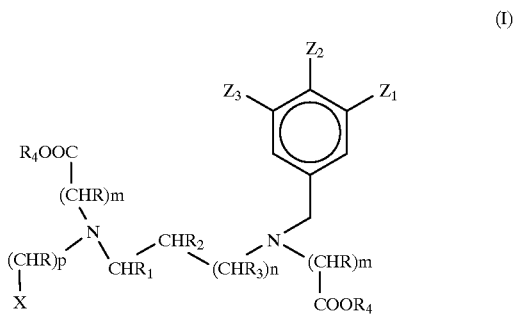

and the salts and metallic complexes thereof are disclosed.

Use in pharmaceutical or cosmetic compositions used to protect the organism from oxidizing stress situations linked to certain pathological states.

1 Claim, No Drawings

DERIVATIVES OF N,N'-DI(CARBOXYALKYL) ALKYLENE DI-OR TRIAMINE

This application claims priority from FR 95 09119, filed Jul. 26, 1995, the entire contents of which is incorporated herein by reference.

The present invention concerns new derivatives of N,N'-di(aralkyl)-N,N'-di(carboxyalkyl) alkylene di- or triamine and of N-(aralkyl)-N'-(carboxyalkyl)-N,N'-di(carboxyalkyl) alkylene di- or triamine, which are used in pharmaceutical or cosmetic compositions to protect the organism against oxidizing stress.

In a number of physiopathological and pathological situations, oxidizing stress is defined as a disequilibrium of the antioxidant-prooxidant balance. This disequilibrium triggers uncontrolled oxidative processes within living tissues, these processes involving oxygenated free radicals and leading, in particular, to oxidative damage on biological molecules and macromolecules.

A number of physiopathological situations cause, promote, accompany, or are the direct consequence of an oxidizing stress, including, most notably, inflammation, aging, exposure to ultra-violet rays and ionizing radiation, carcinogenesis, cases of reperfusion ischemia, toxicity and/or the mode of action of certain drugs.

It has been shown that, during oxidizing stress, iron is released from its habitual storage sites as ferritin and can then take part in certain reactions, in particular the Fenton and Haber-Weiss reactions, which form hydroxyl radicals known to be responsible for extensive oxidative damage.

To ensure protection against hydroxyl radicals, proposals have been made to use molecules such as D-mannitol, benzoic acid, or DMSO, which can trap hydroxyl radicals. However, hydroxyl radicals are particularly reactive, and relatively large quantities of these trapping agents must be used in order to compete with all biological molecules representing potential targets of hydroxyl radicals, a use which raises certain difficulties as a result of the problems of toxicity posed by these trapping agents.

Furthermore, to ensure protection against hydroxyl radicals, a proposal has been made to use iron chelating agents, in particular deferoxamine or diethylene triamine pentacetic acid (DTPA) in order to prevent iron from taking part in the Fenton and Haber-Weiss reactions.

Nevertheless, most of these chelating agents prove to be relatively toxic and can interfere with iron metabolism and chelate the iron of the active sites of certain enzymes or hemoproteins, such as hemoglobin.

Patent Application No. WO 94/11338 proposes the use of certain compounds capable of forming complexes with iron, whose stability constants are low, thereby reducing the risks of toxicity associated with the use thereof.

Patent Application No. WO 94/11338 describes, most notably, the use of certain compounds, which can be represented by the following general formula:

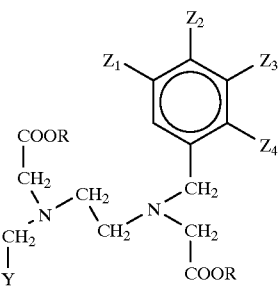

(A)

where:

$Z_1$, $Z_2$ and $Z_3$, whether identical or different, represent an atom of hydrogen, $NO_2$, COOH, $CF_3$, an atom of halogen, or an $OR_1$, $SR_1$, or $NR_1R_2$ group, $R_1$, $R_2$, $R_3$ and $Z_4$, whether identical or different, represent an atom of hydrogen or a linear or branched alkyl radical of $C_1$–$C_8$, and Y represents the radical corresponding to the formula:

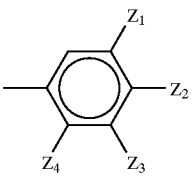

or the radical —COOR and the salts and metal complexes thereof.

After new research on substances which act in accordance with a comparable mechanism, synthesis of a new class of compounds having a better iron-chelating power or better bioavailability, and, in particular, improved solubility, was successfully achieved, a result which could not be obtained using the iron-complexing agents according to prior art.

In fact, it was found, surprisingly and unexpectedly, that increasing the number of carbon atoms between the nitrogen atoms in the compounds corresponding to formula (A) and/or increasing the number of carbon atoms in the lateral carboxylated chains yielded compounds having very clearly improved bioavailability properties, bioavailability leading basically to improved solubility in water and in vehicles widely used in pharmaceutical and/or cosmetic preparations.

It was discovered, moreover, that these new compounds formed, in conjunction with iron, complexes whose association constants were lower than those of known chelating agents, such as deferoxamine. Furthermore, the toxicological risks decreased to the extent that, for thermodynamic reasons, they could not shift the iron from the transferrin.

In addition, the oxidation-reduction potential of the iron in the compounds according to the invention is such that they can be reduced using physiological reductants capable, in reduced form, of reacting with hydrogen peroxide to form hydroxyl radicals that are immediately trapped, in quasi-stoichiometric fashion, by means of an intramolecular aromatic hydroxylation process before they can attack other molecules.

Following intramolecular hydroxylation, these compounds possess an aromatic hydroxy residue capable of occupying a fifth or sixth iron-coordination site. Given the high degree of affinity of phenolate residues for ferric iron, this has the effect of increasing the stability of the complexes by several orders of magnitude and of preventing the subsequent participation of iron in catalysis causing oxidative damage.

The present invention thus concerns, under the heading of new compounds, derivatives of N,N'-di(aralkyl)-N,N'-di(carboxyalkyl) alkylene di- or triamine and of N-(aralkyl)-N'-(carboxyalkyl)-N,N'-di(carboxyalkyl) alkylene di- or triamine, which can be represented by the following general formula:

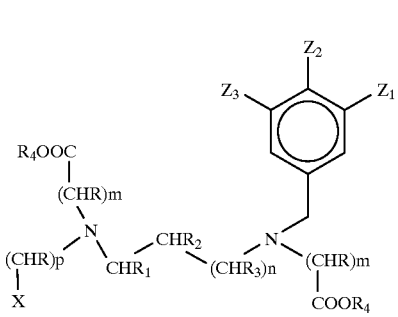

(I)

where:

n is 0, 1, or 2, m and p are 1, 2, or 3,

R, $R_1$, $R_2$, $R_3$, and $R_4$, whether identical or different, represent an atom of hydrogen or a linear or branched alkyl radical of $C_1$–$C_4$, $R_1$ and $R_2$, or $R_2$ and $R_3$ taken together can form a 5- or 6-numbered ring, X represents the radical —$COOR_4$ or the radical corresponding to the formula:

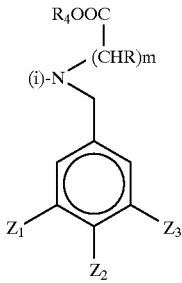

or the radical corresponding to the formula:

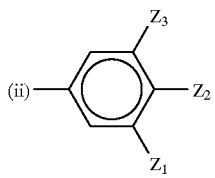

when, in the latter case, p is equal to 1, $Z_1$, $Z_2$, and $Z_3$, whether identical or different, represent an atom of hydrogen, a linear or branched alkyl radical of $C_1$–$C_4$, the radical —$OR_5$ or —$NR_5R'_5$, $R_5$ and $R'_5$ representing an atom of hydrogen or a linear or branched alkyl radical of $C_1$–$C_4$, provided that, when n=0, m=1 and X represents —$COOR_4$ or the radical corresponding to formula (ii), at least one of the radicals R, $R_1$, or $R_2$ is different from an atom of hydrogen, and the salts and metallic complexes thereof.

The expression "linear or branched alkyl radical of $C_1$–$C_4$" signifies radicals such as methyl, ethyl, isopropyl, and tert-butyl.

When $R_1$ and $R_2$ or $R_2$ and $R_3$ taken together form a 5- or 6-membered ring, this ring is a potentially-substituted cyclopentyl or cyclohexyl cycle.

According to a first preferred embodiment of the compounds according to the invention, at least two of the radicals $Z_1$, $Z_2$, and $Z_3$ are different from an atom of hydrogen.

According to a second preferred embodiment of the compounds according to the invention, the radicals $Z_1$, $Z_2$, and $Z_3$ are electron-donor groups and, preferably, represent at least one methoxy group.

Among the salts of the compounds corresponding to formula (I), mention may be made of salts incorporating the addition of a mineral acid such as sulfuric acid, chlorhydric acid, nitric acid, or phosphoric acid, as well as salts incorporating the addition of a mineral or organic base, such as sodium carbonate, potash, or triethanolamine.

Among the complexes, mention may be made of those formed by adding zinc chloride or calcium chloride.

As examples of compounds representing compounds corresponding to formula (I), mention may be made of:

N,N'-bis-(3,4,5-trimethoxybenzyl)-2-methyl ethylenediamine-N,N'-diacetic acid,

N,N'-bis-(3,4,5-trimethoxybenzyl) propylene diamine-N,N'-diacetic acid,

N,N'-bis-(3,5-di-tert-butyl-4-hydroxybenzyl)-2-methyl ethylenediamine-N,N'diacetic acid, N,N'-bis-(3,4,5-trimethoxybenzyl)-1,2-cyclohexyldiamine-N,N'diacetic acid N,N'-bis-(3,4,5-trimethoxybenzyl) ethylenediamine-N,N'-bis(2-methyl) ethyl acetate, N,N'-bis-(3-hydroxy-4-methoxybenzyl) ethylenediamine-N,N'-dipropionic acid, N-(3,5-dimethoxybenzyl) ethylenedimaine-N,N',N'-tripropionic acid, N,N"-bis-(3,4,5-trimethoxybenzyl) diethylene triamine-N,N'N"-triacetic acid, N,N'-bis-(3,4,5-trimethoxybenzyl-2-methylethylenediamine-N,N'-dipropionic acid.

The present invention also concerns the process for preparation of compounds corresponding to general formula (I), which may be represented by the following reaction diagrams I to III:

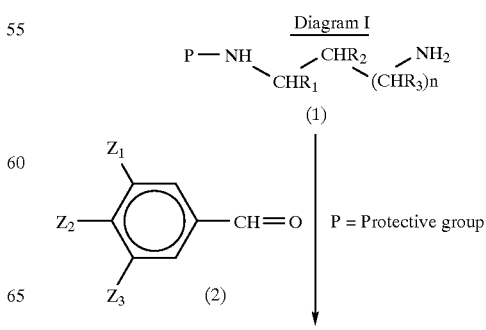

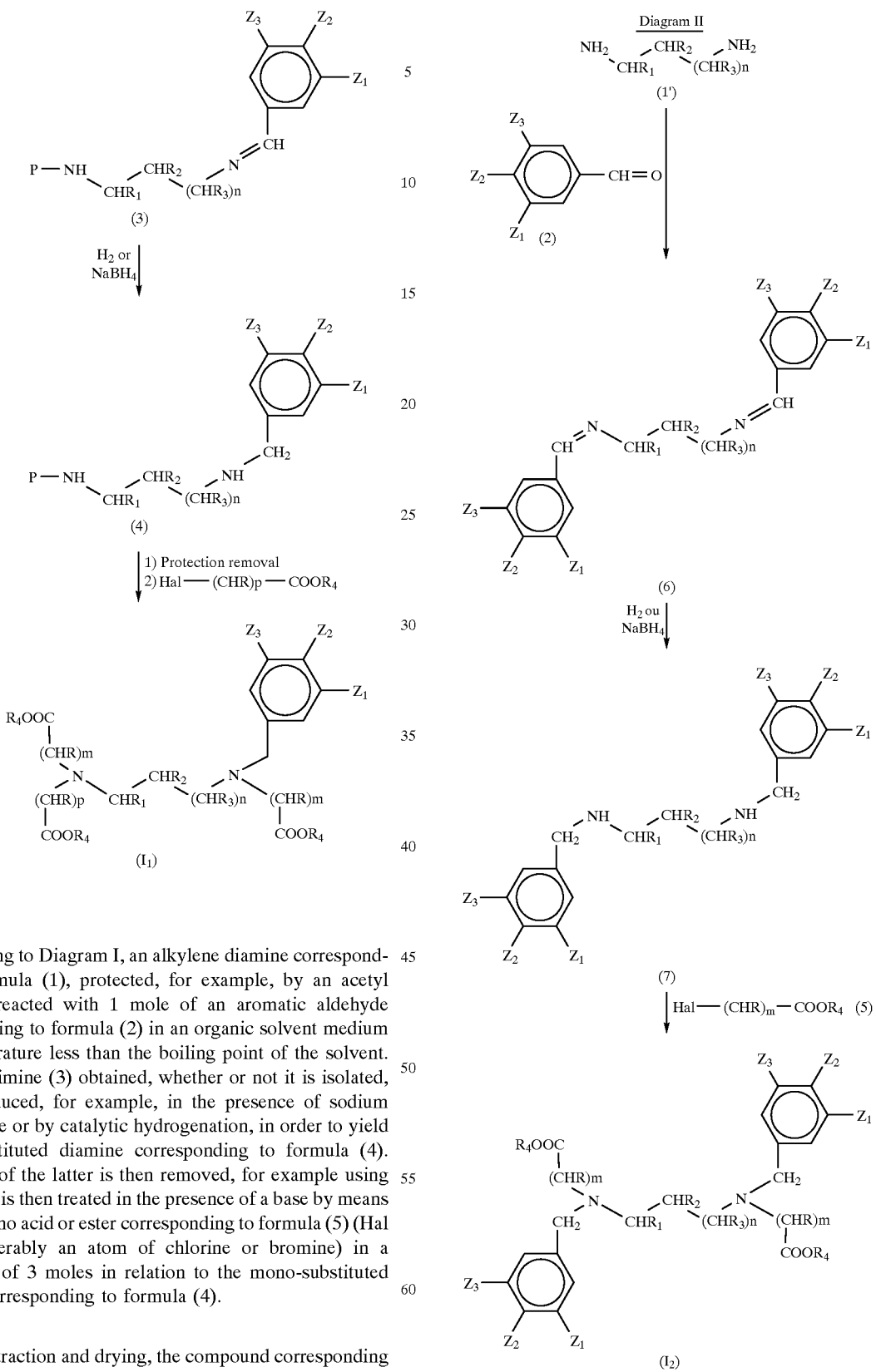

According to Diagram I, an alkylene diamine corresponding to formula (1), protected, for example, by an acetyl group, is reacted with 1 mole of an aromatic aldehyde corresponding to formula (2) in an organic solvent medium at a temperature less than the boiling point of the solvent. The aminoimine (3) obtained, whether or not it is isolated, is then reduced, for example, in the presence of sodium borohydride or by catalytic hydrogenation, in order to yield mono-substituted diamine corresponding to formula (4). Protection of the latter is then removed, for example using HCl, and it is then treated in the presence of a base by means of a halogeno acid or ester corresponding to formula (5) (Hal being preferably an atom of chlorine or bromine) in a proportion of 3 moles in relation to the mono-substituted diamine corresponding to formula (4).

After extraction and drying, the compound corresponding to general formula ($I_1$) is obtained, either in free form or as an acid-added salt, depending on treatment conditions.

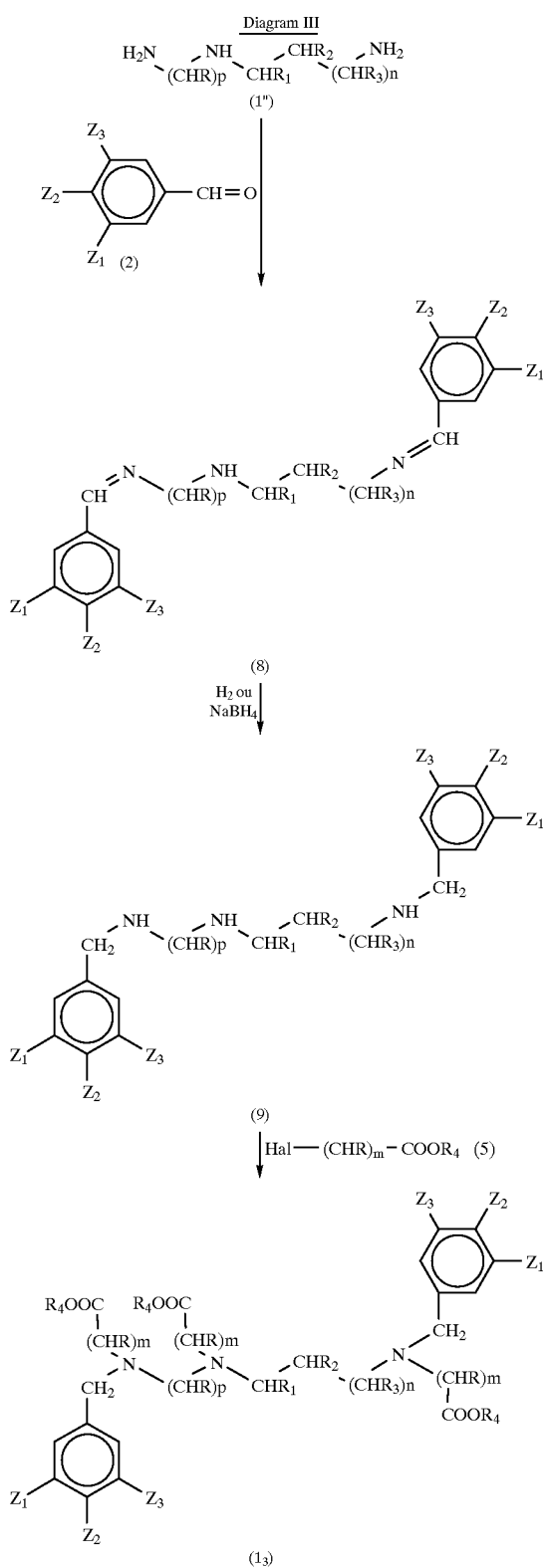

Diagram III

The procedures according to diagrams II and III comprise basically the same steps as the procedure corresponding to Diagram I, except that 2 moles of the aromatic aldehyde compound are reacted for every mole of alkylene di- or triamine corresponding to formula (1') or (1''), as well as 2 or 3 moles halogeno acid or ester corresponding to formula (5) in relation to the amino compounds corresponding to formula (7) and (9).

The present invention further concerns a cosmetic or pharmaceutical composition containing at least one compound corresponding to formula (I) or one of the metallic salts or complexes thereof in a cosmetically- or pharmaceutically-acceptable vehicle.

In these compositions, the active compound corresponding to formula (I) is normally present in a proportion of 0.001 to 10% by weight of the total weight of the composition.

The cosmetic compositions may exist in various conventional forms, such as ointments, creams, pomades, gels, sprays, lotions, emulsions, and vesicular dispersions.

It was found, moreover, that, in the compositions according to the invention, the compound corresponding to formula (I) produced a high level of antioxidant activity and, accordingly, allowed them to be protected from oxidation.

When the compound corresponding to formula (I) is used as part of a pharmaceutical treatment, administration may be made orally, topically, or parenterally, the pharmaceutically-acceptable base depending on the type of administration chosen. Doses normally range between 1 mg and 1,000 mg/kg/day.

The pharmaceutical compositions according to the invention are most especially intended to treat oxidizing stress conditions linked to certain pathological states, and, in particular, neuro-degenerative disorders such as Parkinson's disease, chronic inflammations, reperfusion ischemia syndrome, the toxicity of some drugs, e.g., certain xenobiotics, and iron overloads.

In the compositions according to the invention, the compound corresponding to formula (I) may, in accordance with a preferred embodiment, be combined with at least one other active substance (or other anti-free radical substance). These substances may be chosen more especially from:

anti-lipoperoxidants, such as vitamin E, trolox, and BHT (butyl hydroxytoluene), biological reductants, such as reduced glutathion and the derivatives thereof, vitamin C and the derivatives thereof, singlet oxygen quenchers, such as β-carotene, systems capable of decomposing hydrogen peroxide, and, in particular, enzymes such as catalase or peroxidases in the presence of their co-substrates, superoxide anion-protection systems, such as superoxide dismutase (SOD) or SOD-like systems, such as Mn-deferal or copper di-isopropyl salicylate, systems capable of decomposing organic hydroperoxides, such as glutathion peroxidase, or selenium-based systems.

The compounds corresponding to formula (I) and the active substances or anti-free radical substances such as those specified above may be combined within the same composition, or they may be applied separately.

The following examples are provided in order to illustrate the process for preparation of compounds corresponding to formula (I) and the use thereof in the pharmaceutical and cosmetic fields.

EXAMPLES OF COMPOUND PREPARATION

EXAMPLE 1

Preparation of N,N'-bis-(3,4,5-trimethoxybenzyl)-2-methyl ethylenediamine diacetic acid 1) 40 mmoles 3,4,5-trimethoxybenzaldehyde were solubilized in 30 ml methanol. 20 mmoles 1,2-diaminopropane were added, then the mixture was heated for 30 minutes to 50°. The reactive mixture was concentrated in a vacuum, then reacted directly for the second step.

2) 17 mmoles of the imine obtained in 1), above, were placed in suspension in 100 ml absolute ethanol. 1 sodium borohydride equivalent was added, and the mixture was stirred for one hour at ambient temperature. After evaporation, 20 ml water were added to the residue, and the pH was lowered to 2 by adding chlorhydric acid. The precipitate was then filtered, washed in water, then dried.

3) 10 mmoles of the diamine obtained in step 2), above, were solubilized separately in 15 ml water containing 10 mmoles sodium hydroxide and 20 mmoles bromoacetic acid in 25 ml water at 0° C. containing 30 mmoles sodium monohydrogen carbonate.

The two solutions were mixed and heated to 40° C. for 6 hours, while maintaining the pH at about 12, by adding 30% sodium carbonate.

The mixture was then acidified using concentrated chlorhydric acid until a pH of 4–5 was reached. The solution was concentrated in a vacuum, and the precipitate obtained was filtered. N,N'-bis(3,4,5-trimethoxybenzyl)-2-methyl ethylenediamine diacetic acid was collected in the form of white powder having a melting point of 144° C. and an NMR$^1$H spectrum and ultimate analysis matching the expected structure.

EXAMPLE 2

Preparation of N,N''-bis-(3,5-trimethoxybenzyl) diethylenetriamine-N,N',N''-triacetic acid 1) 60 mmoles 3,4,5 trimethoxybenzaldehyde were solubilized in 100 ml anhydrous toluene. 20 mmoles diethylenetriamine were added, then the mixture was heated to reflux in a three-necked flask fitted with a Dean Stark distillation apparatus until the theoretical quantity of water was distilled. Next, the reactive medium was dry-evaporated, then immediately reacted for the second step.

2) The raw oil obtained in step 1) was solubilized in 100 ml absolute ethanol, then 4 sodium borohydride equivalents were added gradually and the mixture was stirred for 1 hours at 50° C. After evaporation, 20 ml water were added to the residue and the pH was lowered to 1 by adding chlorhydric acid. The precipitate was filtered, washed, then dried. The NMR$^1$H spectrum conformed to the expected triamine structure (77% yield for both steps).

3) 10 mmoles of the triamine obtained in step 2) were solubilized in 150 ml dichloromethane containing 60 mmoles triethylamine. 90 mmoles tertbutyl bromoacetate were added to 250 ml dichloromethane, and the reactive mixture was heated to reflux for 18 hours. The mixture was next cooled, then washed using a dilute chlorhydric acid solution, then a dilute sodium carbonate solution. The organic phase was dried, then concentrated in a vacuum. The oily residue was purified by chromatography on silica. A colorless oil was collected, the NMR$^1$H spectrum of which matched the structure of the tertbutyl triester of N,N''-di(3,4,5-trimethoxybenzyl) diethylenetriamine-N,N',N''-triacetic acid.

4) 1 g of the triester obtained in step 3) was heated to reflux in 100 ml 1M chlorhydric acid for 1 hour. The reactive medium was then dry-evaporated, then washed in cold ethanol and filtered, then dried. This process yielded a white crystallized product whose NMR$^1$H spectrum and ultimate analysis conformed to the structure of the N,N''-di(3,4,5-trimethoxybenzyl) diethylenetriamine-N,N',N''-triacetic acid.

EXAMPLE 3

Preparation of N,N'-bis-(3,4,5-trimethoxybenzyl)-1,3-diaminopropane diacetic acid Using a method similar to that described in Example 1, N,N'-bis-(3,4,5-trimethoxybenzyl)-1,3-diaminopropane diacetic acid was prepared starting with 1,3-diaminopropane. The NMR proton spectrum and ultimate analysis matched the expected structure.

EXAMPLE 4

Preparation of N,N''-bis-(3,4,5-trimethoxybenzyl)-1,2-cyclohexyldiamine-N,N''diacetic acid Using a procedure similar to that in Example 1, N,N'-bis-(3,4,5-trimethoxybenzyl)-1,2-cyclohexyldiamine-N,N-diacetic acid was prepared starting with 1,2-cyclohexyldiamine. A white solid having a melting point of 150° C. (dec.) was obtained, whose NMR$^1$H spectrum (400 MHZ) and ultimate analysis matched the expected structure (existing as a mixture containing 1 H$_2$O, 0.3 HCl and 0.8 HBr.)

|  | C | H | N | O | Cl | Br |
|---|---|---|---|---|---|---|
| Calculated % | 52.65 | 6.60 | 4.10 | 16.38 | 1.56 | 9.36 |
| Found % | 52.69 | 6.81 | 4.03 | 25.74 | 1.42 | 9.34 |

EXAMPLE 5

Preparation of N,N'-bis-(3,4,5-trimethoxybenzyl)-2-methyl ethylenediamine-N,N'-dipropionic acid (a) Ethylic diester of ethylenediamine-N,N'-dipropionic acid 3.9 g thionyl chloride were dripped into a suspension of 1.5 g ethyldiamine-N,N'-dipropionic acid chlorhydrate in 100 ml absolute ethanol. The mixture was heated to 75° C. for 24 hours. The mixture was filtered under heat, then the mother solutions were cooled. The solid formed was filtered, then washed with ethanol. After recrystallization in 15 ml ethanol, a white solid was produced whose NMR$^1$H spectrum matched the expected structure (in the form of dichlorhydrate).

(b) Ethylic diester of N,N'-bis-(3,4,5-trimethoxybenzyl)-ethylenediamine-N,N'-dipropionic acid A mixture of 1 g dichlorhydrate of the ethylic diester of ethylenedimaine-N,N'-dipropionic acid, 0.9 ml triethylamine, 0.75 g of CaCO$_3$, and 1.6 g 3,4,5-trimethoxybenzyl chloride was heated to 80° C. for 4 hours. After cooling, the mixture was dry-evaporated and taken up in 50 ml water. The solution was acidified until a pH of 1 was reached using concentrated HCl, then extracted using 3×25 ml dichloromethane. The organic phase was washed in water saturated with NaCl, then dried and dry-evaporated. The oil produced was purified by chromatography on a silica column (98:2 dichloromethane/methanol eluant). 0.6 g of an oil was obtained, whose NMR$^1$H (400 MHZ) corresponded to the structure of the ethylic diester of N,N'-bis-(3,4,5-trimethoxybenzyl)-ethylenediamine-N,N'-dipropionic acid.

(c) N,N'-bis-(3,4,5-trimethoxybenzyl)-2-methyl ethylenediamine-N,N'-dipropionic acid 2.2 g ethylic diester of N,N'-bis-(3,4,5-trimethoxybenzyl) ethylenediamine-N,N'-dipropionic acid were solubilized in a mixture of 20 ml 1N NaOH and 40 ml methanol. The mixture was stirred for 2 hours at ambient temperature.

The solution was dried, then taken up in 25 ml water.

After washing in 3×25 ml dichloromethane, the aqueous phase was acidified to a pH of 4.5 using concentrated HCl, then dry-evaporated. 25 ml ethanol were then added, and the mixture was cooled to 0° C. The salts were removed by filtration, then the solution was concentrated to a volume of 5 ml. 0.5 ml 0.8N HCl was then added, and the mixture was stirred for 1 hour. The solid obtained was next filtered, then rinsed in ethylic ether.

200 mg of a white powder having a melting point of 220° C. (dec.) were obtained, whose NMR$^1$H spectrum (400 MHZ) and ultimate analysis matched the expected structure (in the form of dichlorohydrate).

|  | C | H | N | O | Cl |
|---|---|---|---|---|---|
| Calculated % (with 2 H$_2$O and 0.7 NaCl) | 47.06 | 6.44 | 3.92 | 26.89 | 13.43 |
| Found % | 46.95 | 6.54 | 3.94 | 26.41 | 12.33 |

COMPARATIVE SOLUBILITY TESTS

| Compounds | Solvent 50 mM Acetate Buffer pH 5.8 |
|---|---|
| N,N'-bis-(3,4,5-trimethoxybenzyl) 2-methyl ethylenediamine N,N'-diacetic acid, 2 HCl | >10% |
| N,N'-bis-(3,4,5-trimethoxybenzyl) ethylenediamine-N,N'-diacetic acid, 2 HCl (Compound in accordance with WO 94/11338) | <0.5% |

FORMULATION EXAMPLES
I. COSMETIC

EXAMPLE A

Using conventional methods, an emulsion was prepared using the following constituents:

| | |
|---|---|
| N,N'-bis-(3,4,5-trimethoxybenzyl)-2-methyl ethylenediamine diacetic acid (compound in Example 1) | 0.1 g |
| 50 moles oxyethylenated polyethylene glycol | 3.0 g |
| Mono/diglyceryl stearate | 3.0 g |
| Vaseline oil | 24.0 g |
| Cetyl alcohol | 5.0 g |
| Water qsp | 100.0 g |

EXAMPLE B

An emulsion was prepared in accordance with conventional techniques using the following constituents:

| | |
|---|---|
| N,N'-bis-(3,4,5-trimethoxybenzyl)-2-methyl ethylenediamine diacetic acid (compound in Example 1) | 0.5 g |
| Octyl palmitate | 10.0 g |
| Glyceryl isostearate | 4.0 g |
| Vaseline oil | 24.0 g |
| Vitamin E | 1.0 g |
| Glycerol | 3.0 g |
| Water qsp | 100.0 g |

EXAMPLE C

The following composition was prepared using conventional techniques using the constituents listed below:

| | |
|---|---|
| N,N'-bis-(3,4,5-trimethoxybenzyl)-2-methyl ethylenediamine diacetic acid (compound in Example 1) | 0.10 g |
| Jojoba oil | 13.00 g |
| Potassium sorbate | 0.30 g |
| Cyclopentadimethylsiloxane | 10.00 g |
| Stearyl alcohol | 1.00 g |
| Stearic alcohol | 4.00 g |
| Polyethylene glycol stearate | 3.00 g |
| Vitamin E | 1.00 g |
| Glycerol | 3.00 g |
| Preservatives | 0.05 g |
| Water qsp | 100.00 g |

When regularly applied once daily, preferably in the evening, the compositions in Examples A to C, above, make it possible to prevent skin aging in an especially significant way. It was found, moreover, that these compositions exhibited excellent stability over time, since the active compound protected them from oxidation phenomena.

In these compositions, the compound in Example 1 may advantageously be replaced with the same quantity of one of the compounds in Examples 2, 3, 4, and 5.

II. PHARMACEUTICAL

EXAMPLE A: Oral Administration

1) Pill

| | |
|---|---|
| N,N'-bis-(3,4,5-trimethoxybenzyl)-2-methyl ethylenediamine diacetic acid (compound in Example 1) | 0.001 g |
| Starch | 0.114 g |
| Bicalcium phosphate | 0.020 g |
| Lactose | 0.060 g |
| Magnesium stearate | 0.005 g |

2) Drinkable Suspension

| | |
|---|---|
| N,N'-bis-(3,4,5-trimethoxybenzyl)-2-methyl ethylenediamine diacetic acid (compound in Example 1) | 0.001 g |
| Glycerol | 0.500 g |
| 70% sorbitol | 0.520 g |
| Sodium saccharinate | 0.010 g |
| Methyl p-hydroxybenzoate | 0.040 g |
| Flavoring qs | |
| Purified water qsp | 5 ml |

3) Drinkable Suspension

| | |
|---|---|
| N,N''-bis-(3,4,5-trimethoxybenzyl) diethylenetriamine-N,N'N''-triacetic acid (compound in Example 2) | 0.100 g |
| 90% ethanol | 1.000 g |
| 70% sorbitol | 0.500 g |
| Sodium saccharinate | 0.010 g |
| Methyl p-hydroxybenzoate | 0.040 g |
| Flavoring qs | |
| Purified water qsp | 5 ml |

When given in suitable doses 1 to 2 times a day for about 3 to 5 weeks, formulations 1) to 3), above, allow effective treatment of the majority of neurodegenerative diseases.

In formulations 1) and 2), the compound in Example 1 may advantageously be replaced with the same quantity of one of the compounds in Examples 3, 4, and 5.

In formulation 3), the compound in Example 2 may advantageously be replaced with the same quantity of one of the compounds in Examples 1, 4, and 5.

EXAMPLE B: Administration by Injection

| 3 ml Injectable Vial | |
|---|---|
| N,N'-bis-(3,4,5-trimethoxybenzyl)-2-methyl ethylenediamine diacetic acid (compound in Example 1) | 0.005 g |
| Sodium bicarbonate | 0.001 g |
| Water for injectable preparation qsp | 3 ml |

In this example of a formulation prepared as an injectable vial, the compound in Example 1 may advantageously be replaced by the same quantity of one of the compounds in Examples 2, 3, and 5.

We claim:

1. A compound selected from the group consisting of

N,N'-bis-(3,4,5-trimethoxybenzyl)-2-methylethylene diamine-N,N'-diacetic acid,

N,N'-bis-(3,4,5-trimethoxybenzyl) Propylene diamine-N,N'-diacetic acid,

N,N'-bis-(3,5-di-tert-butyl-4-hydroxy-benzyl)-2-methyl ethylenediamine N,N'-diacetic acid, N,N'-bis-(3,4,5-trimethoxybenzyl)-1,2-cyclohexyldiamine-N,N'diacetic acid, N,N'-bis-(3,4,5-trimethoxybenzyl) ethylenediamine-N,N'-bis(2-methyl) ethyl acetate, N,N'-bis-(3-hydroxy-4-methoxybenzyl) ethylenediamine-N,N'-dipropionic acid, N-(3,5-dimethoxybenzyl) ethylenediamine-N,N',N'-tripropionic acid, N,N''-bis-(3,4,5-trimethoxybenzyl) diethylene triamine-N,N'N''-triacetic acid, N,N'-bis-(3,4,5-trimethoxybenzyl)-2-methyl ethylenediamine-N,N'-dipropionic acid, and the salts and metallic complexes thereof.

* * * * *